(12) United States Patent
Prabhakar et al.

(10) Patent No.: US 8,715,558 B2
(45) Date of Patent: May 6, 2014

(54) CAPILLARY ELECTROPHORESIS CHIPS

(75) Inventors: Amit Prabhakar, Bihar (IN); Soumyo Mukherji, Kolkata (IN)

(73) Assignee: Indian Institute of Technology Bombay, Mumbai (IN)

( * ) Notice: Subject to any disclaimer, the term of this patent is extended or adjusted under 35 U.S.C. 154(b) by 137 days.

(21) Appl. No.: 13/257,948

(22) PCT Filed: Oct. 1, 2010

(86) PCT No.: PCT/IB2010/002496
§ 371 (c)(1),
(2), (4) Date: Sep. 20, 2011

(87) PCT Pub. No.: WO2011/138635
PCT Pub. Date: Nov. 10, 2011

(65) Prior Publication Data
US 2012/0193234 A1 Aug. 2, 2012

(30) Foreign Application Priority Data
May 3, 2010 (IN) .................. 1407/MUM/2010

(51) Int. Cl.
*B29C 41/42* (2006.01)
(52) U.S. Cl.
USPC ........... 264/336; 264/236; 264/313; 264/317; 264/334
(58) Field of Classification Search
USPC ..................... 264/236, 313, 317, 334, 336
See application file for complete search history.

(56) References Cited

U.S. PATENT DOCUMENTS

| | | | | |
|---|---|---|---|---|
| 4,459,257 A * | 7/1984 | Baciu | ............ | 264/255 |
| 6,659,756 B2 * | 12/2003 | Strait et al. | ............ | 425/222 |
| 2002/0134907 A1 * | 9/2002 | Benett et al. | ............ | 249/135 |
| 2003/0203366 A1 * | 10/2003 | Lim et al. | ............ | 435/6 |
| 2005/0217990 A1 * | 10/2005 | Sibbett et al. | ............ | 204/252 |
| 2010/0046902 A1 * | 2/2010 | Kaplan et al. | ............ | 385/129 |
| 2010/0063404 A1 * | 3/2010 | Kaplan et al. | ............ | 600/478 |
| 2010/0064784 A1 * | 3/2010 | Caudill et al. | ............ | 73/105 |

(Continued)

FOREIGN PATENT DOCUMENTS

| | | |
|---|---|---|
| WO | WO/00/58721 | 10/2000 |
| WO | WO 01/96958 | 12/2001 |

(Continued)

OTHER PUBLICATIONS

Yang et al. "Fabrication of SU-8 embedded microchannels with circular cross-section". 2004. International Journal of Machine Tools & Manufacture 44. pp. 1109-1114.*

(Continued)

*Primary Examiner* — Matthew Daniels
*Assistant Examiner* — Saeed Huda
(74) *Attorney, Agent, or Firm* — Workman Nydegger

(57) ABSTRACT

A seamless microchannel with aligned microelectrodes structure can be prepared to include a polymeric body defining a surface of a seamless microchannel. The microchannel is seamless in that it is formed by a single body of material having a conduit that is open at one surface and extends to another opening aligned with microelectrodes in another surface of the body. The rest of the microchannel is closed and defined by the single body of material. The seamless microchannel structure can be used in methods that include biosensors, coupling waveguides, capillary electrophoresis chips, microreactors, polymerase chain reaction-chips, and solving mathematical problems.

13 Claims, 11 Drawing Sheets

(56) References Cited

U.S. PATENT DOCUMENTS

| | | | |
|---|---|---|---|
| 2010/0068740 A1* | 3/2010 | Kaplan et al. | 435/14 |
| 2010/0070068 A1* | 3/2010 | Kaplan et al. | 700/159 |
| 2010/0096763 A1* | 4/2010 | Kaplan et al. | 264/1.1 |
| 2010/0120116 A1* | 5/2010 | Kaplan et al. | 264/1.1 |

FOREIGN PATENT DOCUMENTS

| | | | |
|---|---|---|---|
| WO | WO 2007/115694 | | 10/2007 |
| WO | WO 2008/127403 | * | 10/2008 |
| WO | WO 2008/127405 | * | 10/2008 |

OTHER PUBLICATIONS

Verma et al. "Embedded Template-Assisted Fabrication of Complex Microchannels in PDMS and Design of a Microfluidic Adhesive". 2006. Langmuir. pp. 10291-10295.*

"A micromachined capillary electrophoresis chip with fully integrated electrodes for separation and electrochemical detection," R Wilke and S Büttgenbach, Biosensors and Bioelectronics, vol. 19, Issue 3, Nov. 30, 2003, pp. 149-153.

Richard P. Baldwin, et al. "Fully Integrated On-Chip Electrochemical Detection for Capillary Electrophoreses in Microfabricated Device", Anal. Chem. 2002, 74, 3690-3697.

Gang Chen, et al. "Fabrication and performance of a three-dimensionally adjustable device for the amperometric detection of microchip capillary electrophoresis" Electrophoresis 2005, 26, 4632-4640.

Min Zhong, et al. "Dual-Electrode Detection for Capillary Electrophoresis/Electrochemistry" Anal. Chem. 1996, 68, 203-207.

Frank-Michael Matysik "Studies on Water-Resistant Dye Compounds by Means of Nonaqueous Capillary Electrophoresis with Electrochemical Detection" Electroanalysis 1999, 11, No. 14, 1017-1021.

Perry et al., "Simple fabrication technique for rapid prototyping of seamless cylindrical microchannels in polymer substrates", Review of Scientific Instruments, vol. 78, online Apr. 17, 2007, pp. 044302.

International Search Report and Written Opinion from International Application No. PCT/IB2010/002496 dated Mar. 11, 2011.

* cited by examiner

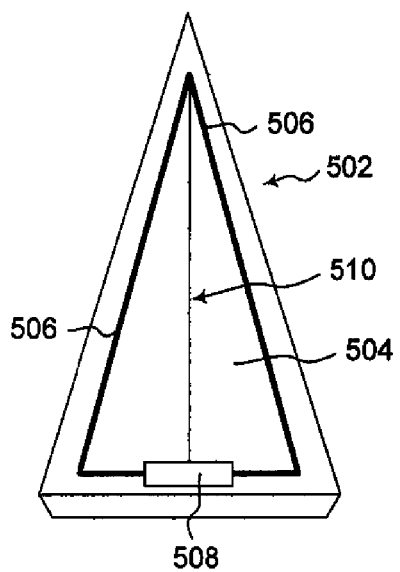 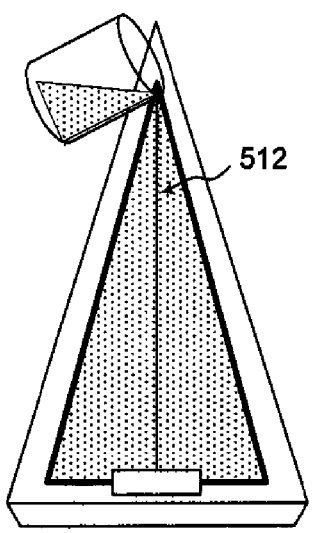 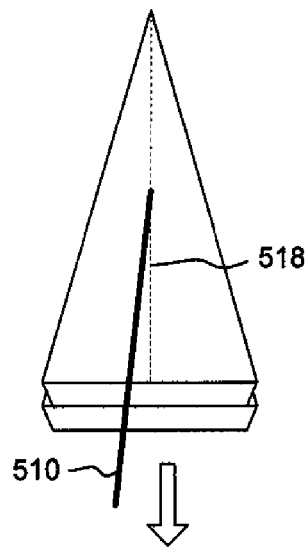
Figure 5A  Figure 5B  Figure 5C
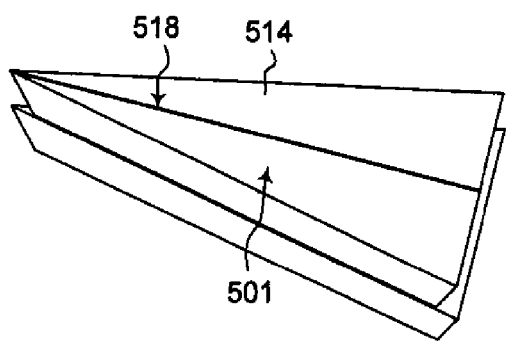
Figure 5D

CAPILLARY ELECTROPHORESIS CHIPS

This application is a U.S. Nationalization of PCT International Application No. PCT/IB2010/002496, filed 1 Oct. 2010, entitled "CAPILLARY ELECTROPHORESIS CHIPS," which claims priority Indian Patent Application No. 1407MUM/2010, filed 3 May 2010, the entireties of both of the foregoing applications are incorporated herein by reference.

BACKGROUND

Microchannel devices and systems have various applications that utilize the fluid properties in small cross-sectional dimensioned conduits. These small conduits can be favorably applied for minimum volume sample handling and fast detection response for sample analysis. Examples of uses for microchannel devices and systems can include, but are not limited to, biosensors, coupling waveguides, capillary electrophoresis chips, microreactors, polymerase chain reaction-chips, and solving mathematical problems.

However, manufacture of microchannel structures can be complicated and tedious. Also, manufacture methods may result in microchannel structures that have seams or include multiple members affixed (e.g., adhesive or bonding) together. These seams and junctions can cause imperfections in the microchannel that alter the dimensions of the conduit, which is unfavorable for micron scale applications. Also, these seams and junctions can be susceptible to failure during use.

An example of a conventional method for manufacturing microchannel systems is the use of lithography, in which three-dimensional channel patterns are first generated on a substrate using a series of processes, such as photo exposure, development, baking, etching, and the like, after which a microchannel is formed with one sidewall open so as to have a "U" like shape. The process for closing the microchannel so that only the entrance and exit of the microchannel is open can include aligning the microchannel structure with a flat substrate and then fusing or chemically bonding the microchannel structure with the flat substrate. Although current microchannel manufacturing techniques can provide microchannel structures on both stiff (e.g., glass and silicon) and soft (e.g., poly(dimethylsiloxane) or PDMS) materials, these structures have seams or junctions between different materials or structure portions. As such, these structures can have imperfections that are not favorable for many applications of microchannels due to the seams or junctions. For example, the methods produce microchannel structures that can have misalignment that results in unsuitable and varied dimensions and/or failure of the seal at the interface of two body members, which may result in leakage from the microchannel.

SUMMARY

In one aspect, a microchannel structure can include a polymeric body defining a surface of a seamless microchannel. The microchannel is seamless in that it is formed by a single body of material having a conduit that is open at one surface and extends to another opening in the same or another surface of the body. The microchannel can include a cross-sectional dimension in the micro scale range or smaller, which can include nano scale dimensions. The rest of the microchannel is closed and defined by the single body of material. The microchannel structure can be used in methods that include, but are not limited to, biosensors, coupling waveguides, capillary electrophoresis chips, microreactors, polymerase chain reaction-chips, and solving mathematical problems.

In one aspect, a method of manufacturing can produce a microchannel structure with a seamless microchannel therein. Such a method can include providing a vessel having a body defining an internal chamber that has at least a first opening and a second opening; introducing a micron scale or smaller dimensioned wire within the internal chamber; polymerizing a polymerizable composition within the internal chamber around the wire; removing the wire from the polymerizable composition before full polymerization so as to leave a microchannel in a shape stable polymer; and completing the polymerization to form a polymeric body defining the microchannel.

In another aspect, a method of manufacturing can produce a capillary electrophoresis structure having a seamless microchannel. Such a method can include forming the microchannel structure using a vessel having an internal chamber with two open ends and a wire passing through the internal chamber and out of both the open ends. A polymerizable composition can be placed in the internal chamber around the wire and partially polymerized until shape stable so that the wire can be removed to leave channel within the polymerizing body. The shape stable polymerizing body can be identified by the polymerizing body having elasticity and shape memory such that the body returns to the original shape after being touched or pressed and such that the channel is retained as a fluid passageway. The method can also include positioning one or more electrodes within the polymeric body and optionally the internal chamber so as to be operably coupled with the microchannel. This can include forming one or more electrode receiving openings in the vessel before, during or after polymerization, and placing electrodes within the receiving openings so as to extend into the internal chamber. The one or more openings can be formed in the vessel with a drill, punch, hot wire, laser, or the like. The one or more openings can extend into a reservoir within the vessel, which reservoir is a void space between the vessel and the polymeric body of the microchannel structure and which has one opening operably coupled within the reservoir.

In another aspect, a microcapillary electrophoresis device can be prepared to include a microchannel structure having a seamless microchannel as described herein. The method of preparing a microcapillary electrophoresis device can include preparing a microchannel structure and operably coupling microcapillary electrophoresis components with the microchannel structure.

In one aspect, a microcapillary electrophoresis kit can include a microcapillary structure having a seamless microchannel and one or more microcapillary electrophoresis components.

In one aspect, a microcapillary electrophoresis system can include a microcapillary structure having a seamless microchannel that is operably coupled with one or more microcapillary electrophoresis components.

In one aspect, the microchannel structure can be associated with a microcapillary electrophoresis system configured for use in a method of detection of an analyte. Such a method can include providing a microcapillary electrophoresis system that includes a microchannel structure having a seamless microchannel; electrophoresing an analyte through the microchannel; and detecting an electronic property of the analyte.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 1A-1G illustrate an embodiment of a method for preparing an example of a microcapillary electrophoresis device having a microchannel structure.

FIGS. 5A-5D illustrate an embodiment of a method for preparing a microchannel structure.

DETAILED DESCRIPTION

Figure 1B:
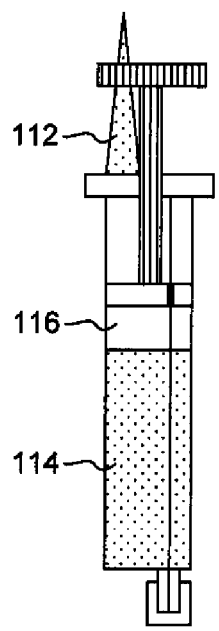

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used herein, a "body" is meant to refer to a physical structure that is used to form a microchannel structure as described herein. A body can have any three-dimensional shape of appropriate size suitable for having a microchannel therein. A "polymeric body" is a body that is made of a polymeric material, and which can be formed by polymerization of suitable monomers.

As used herein, a "channel" is meant to refer to a pathway or conduit that is at least partially defined by at least one wall. A channel can also be referred to as a conduit, passage, pipe, route, tunnel, lumen, or the like. A channel can be closed and have one or more openings for accessing the channel. A channel can be open such that the length of the channel is open from one opening to the opposite opening.

As used herein, a "microchannel" is means to refer to a channel having a micron scale or smaller dimension, such as diameter, height, or width, of a cross-sectional profile. The "microchannel" can have a nano scale or smaller dimension, such as diameter, height, or width. Thus, a microchannel can have a cross-sectional dimension that is on the micron scale or smaller.

As used herein, a "microchannel structure" is the body that defines and contains the microchannel therein. As such, the microchannel structure has two or more openings in the body that each opens into the microchannel structure.

As used herein, a "seam" is meant to refer to an intersection that joins two surfaces together, whereby the junction is the seam between the two abutting surfaces or edges. The two surfaces or edges can be from the same body or from two different bodies. The term "seam" can also be referred to as a bond, closure, connection, coupling, joint, junction, junction, or union. Seams can be formed by coupling the two abutting surfaces or edges, such as, without limitation, glue, adhesive, brazing, or other type of coupling.

As used herein, "seamless" is meant to refer to a body or body portion that does not have a seam. A seamless microchannel can have a smooth, continuous surface that defines the microchannel. Accordingly, a single body can be used to form a seamless microchannel located within the single body, such that a channel of a micron scale or smaller extends from a first opening to a second opening in the body with a passageway therebetween.

As used herein, a "channel surface" is meant to refer to a surface of a body that defines a channel. A "seamless channel" has a single, continuous surface that defines the channel.

As used herein, a "microchannel forming member" is meant to refer to an elongate member that is used to form a channel when a polymerizable composition is polymerized around the elongate member. The elongate member can be linear without any bends or branches. Alternatively, the elongate member can be prepared to have one or more bends such that the elongate member forms a microchannel with one or more curves in the channel. The elongate member may be formed into a member with one or more branches or can be coupled or associated with one or more additional elongate members such that the branched elongate member(s) forms a branched microchannel with one or more channels that intersect and channel junctions. The elongate member can be flexible or rigid. Examples of elongate members can include wire, thread, filament, or other similarly configured elongate bodies.

As used herein, a "vessel" is meant to refer to a hollow, concave, or walled chamber that can receive and hold a polymerizable liquid. The vessel can be configured as a container, tray, or walled substrate that is open or closed. The vessel can be any suitable reaction container for conducting a polymerization reaction. The vessels can range from bench-top sizes through industrial scale sizes. The shapes can be any three-dimensional shape configured to hold a polymerizable liquid.

As used herein, an "internal chamber" is meant to refer to a cavity within a vessel as described herein. The internal chamber is the internal space defined by the vessel. The internal chamber may have one or more openings that extend through the walls of the vessel.

As used herein, "fluidly coupled" is meant to refer to a coupling through a channel or conduit that allows fluids (e.g., gases and liquids) to flow therethrough or therebetween. For example, a microchannel can fluidly couple a reservoir at one opening of the microchannel with a reservoir at another opening of the microchannel.

In one embodiment, a polymeric body can be configured to define a microchannel that is located within the polymeric body. As such, a surface of the polymeric body can form the surface of the microchannel. The microchannel can be configured similar to a lumen such that a single, continuous surface of the polymeric body is the surface of the microchannel which has two or more openings. For example, the microchannel can be linear or straight and extend from a first opening in the polymeric body to an opposite, second opening in the polymeric body. The polymeric body that defines the microchannel can be referred to as a microchannel structure.

In one embodiment, the microchannel structure can be a microchannel structure that has a seamless microchannel. As such, the microchannel is seamless so as to be defined by a continuous microchannel surface that is devoid of any seam or junction between two surfaces or edges. For example, the microchannel can be configured as a lumen that extends between two or more openings in the microchannel structure, and where there are no seams in the microchannel surface. A single polymeric body can include a seamless channel therein that is configured to have a micron scale dimension. While the microchannel structure may have a body with one or more seams, such seams do not intersect the seamless microchannel.

In one embodiment, the microchannel structures can be used in devices that include, but are not limited to, biosensors, coupling waveguides, capillary electrophoresis chips, microreactors, and polymerase chain reaction chips, and for solving mathematical problems.

The microchannel structure (e.g., having a seamless microchannel) can be included in a microcapillary electrophoresis device for electrochemical detection. The microcapillary electrophoresis device can be used for voltometry, conductometry, amperometry or potentiometry principle based chips. All electronic variants of electrochemical detection means are intrinsically simpler than the optical methods. End-column amperometric detection is found to be more sensitive and more commonly used among all types.

Electrochemical detection, such as voltometry, conductometry, amperometry, or potentiometry, is attractive for analyte analysis. Electrochemical detection methods are intrinsically simpler than optical methods. An electrical signal is obtained directly without the involvement of an intermediate physical parameter, such as radiation intensity in optical methods. The detector hardware consists of three or fewer small electrodes and relatively simple electronic circuitry, whereas for optical detection, a light source, monochromator, optical detectors and focusing optics are necessary. In optical methods, the cell volume directly affects the signal via the optical path length and, for this reason, the capillary diameters are as large as possible. For electrochemical detection, the cell size (sample volume) has only a direct bearing in conductivity measurements. In amperometry, the signal is related to the area of the working electrode, the size of which will be limited by the available sample volume. For potentiometric detection, the signal is independent of the sensor size and, therefore, of the cell volume and capillary diameter. Conductivity detection can be regarded as a universal method, while amperometric detection is restricted to electroactive species, and potentiometric detection is not possible for certain small ions with multiple charges. Very low detection limits have been reported for amperometric detection.

For simplicity and ease of following the figures, elements introduced into a device or component with element numbering in one figure may be assumed to be present if illustrated in another the device or component shown in another figure. Also, elements introduced into a device or component in one figure may be present if illustrated into a similar device or component in another figure even if not labeled with an element number.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

FIGS. 1A-1G illustrate an embodiment of a method for preparing an example of a microcapillary structure having a microchannel therein. FIG. 1A shows a vessel (e.g., syringe) 100 having a plunger 102 and a removable cap 104 sealing one end of an internal chamber 106 between the plunger 102 a port 105. The vessel 100 is shown to have an opening 108 in a plunger head 103 that receives a wire 110 that extends from the plunger head 103 to the port 105. The wire 110 can be affixed to the plunger head 103 by tape or adhesive. The wire 110 can also be affixed or sealed to the port 105 by the removable cap 104 or by tape or adhesive.

FIG. 1B shows a polymerizable composition 112 being introduced into the internal chamber 106 of the vessel 100. The polymerizable composition 112 can pass through the opening 108 or drawn in through the port 105 by actuating the plunger 102, or another opening (not shown) can be formed in the vessel 100 or plunger head 103 for receiving the polymerizable composition 112. The polymerizable composition 112 is polymerized (at least partially) in the internal chamber 106 and around the wire 110 to form a polymeric body 114. An electrode space 116 is formed between the plunger head 103 and the polymeric body 114.

Figure 1C:
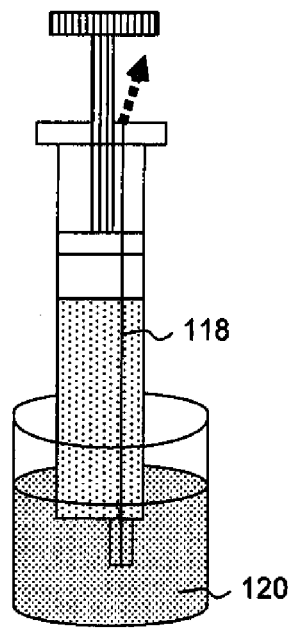

FIG. 1C shows that after at least some polymerization, the wire 110 can be removed from the polymeric body 114 to result in a microchannel 118. For example, the wire 110 can be pulled (shown by dashed arrow) from the polymeric body 114 through the opening 108. Also, a solvent 120 can be introduced into the port 105 during the removal of the wire 110 to function as a lubricant.

Figure 1D:
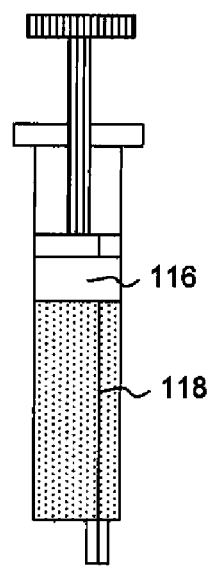

FIG. 1D shows the microchannel 118 within the polymeric body 114 extending from the port 105 to the electrode space 116.

Figure 1E:
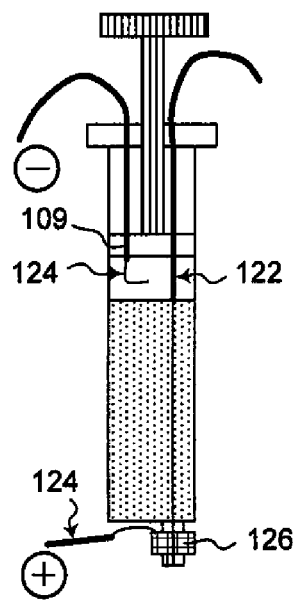

FIG. 1E shows a detection electrode 122 extending into the internal chamber 106 through the opening 108 in the plunger head 103. Also, electrophoresis electrodes 124 are shown to be positioned relative to the microchannel 118 at opposing ends, which can pass through another opening 109 in the plunger head 103 and through the port 105. A fastener 126 (e.g., o-ring) can attach the electrophoresis electrode to the vessel 100 at the port 105.

Figure 1F:
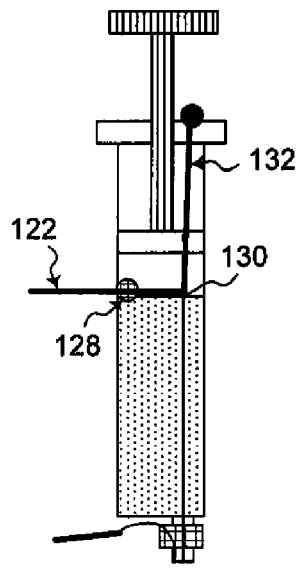

FIG. 1F shows another detection electrode 122 inserted into the internal chamber 106 through an opening 128. The detection electrode 122 is positioned to be proximal to an opening 130 in the microchannel 118 that opens into the electrode space 116. An alignment wire 132 can be used for positioning of the detection electrode 122. The Alignment wire 132 may be the same wire used for making the channel or can be inserted into the channel ending after the channel formation and it can help in planer alignment of working electrode with micro-channel in following way. The working electrode will be introduced inside the hole of syringe wall just gliding over polymer layer and its tip will be made in contact with the alignment wire just coming out of the channel. This contact can be tested by testing the electrical connectivity between the working electrode's contact wire and alignment wire. In this way the working electrode tip will be just at the end and in the plane with the floor of microchannel ending.

Figure 1G:
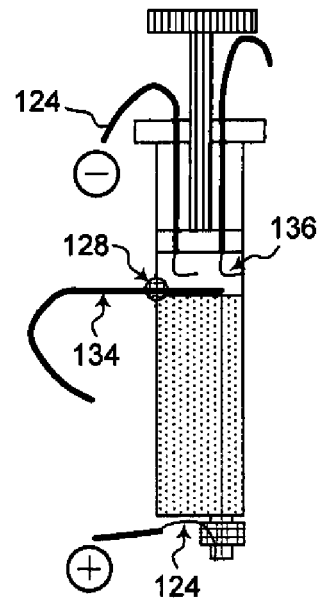

FIG. 1G shows a working electrode 134 positioned in the opening 128 and adjacent to the opening 130 of the microchannel 118 in the electrode space 116. A counter electrode 136 is also positioned in the electrode space 116 via the opening 108 so as to be operably coupled with the working electrode 134. Accordingly, the device in FIG. 1G can be used in microcapillary electrophoresis.

Figure 2A:
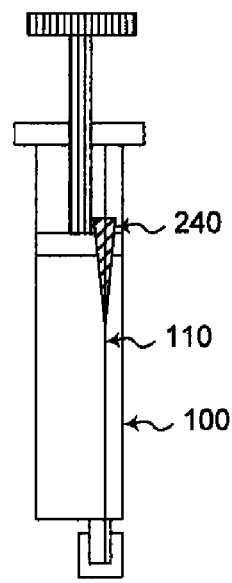
FIGS. 2A-2D illustrate an embodiment of a method for preparing an example of a microcapillary electrophoresis device having a microchannel structure.
Figure 2B:
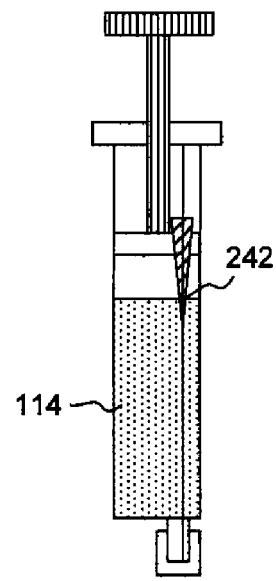
Figure 2C:
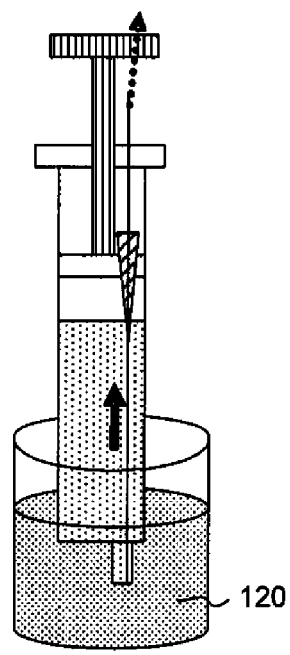
Figure 2D:
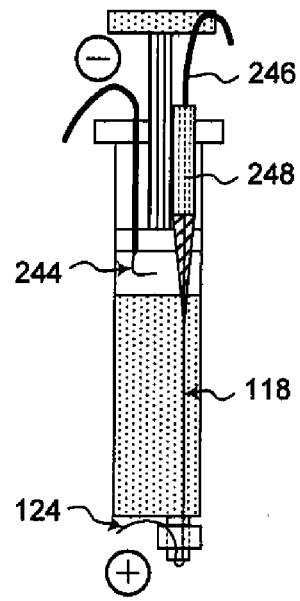

FIGS. 2A-2D illustrate another embodiment of a method for preparing an example of a microcapillary electrophoresis device having a microchannel structure, which is similar to the method of FIGS. 1A-1G, and uses some of the components thereof. FIG. 2A shows a guide member 240 (e.g., pipette tip) is inserted into the opening 108 of the plunger head 103 of the vessel 100. FIG. 2B shows that a polymerizable composition (not shown) is introduced into the vessel 100 up to the guide member 240, to form a polymeric body 114, such that the guide member 240 intersects the polymeric body 114 at a junction 242. FIG. 2C shows a solvent 120 being used during the withdrawal of the wire 110 from the vessel 100, which is shown by the dashed arrow. FIG. 2D shows that an electrode 244 that functions as a cathode and counter electrode. Also, the guide member 240 can be configured to be or replaced by a detection electrode 248 having a detection wire 246. The detection electrode 248 contacts or is adjacent to the opening 130 of the microchannel 118. Accordingly, the device in FIG. 2D can be used in microcapillary electrophoresis.

Figure 3A:
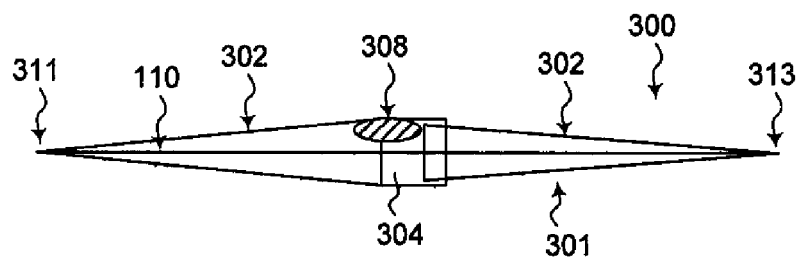
FIGS. 3A-3F illustrate an embodiment of a method for preparing an example of a microcapillary electrophoresis device having a microchannel structure.
Figure 3B:
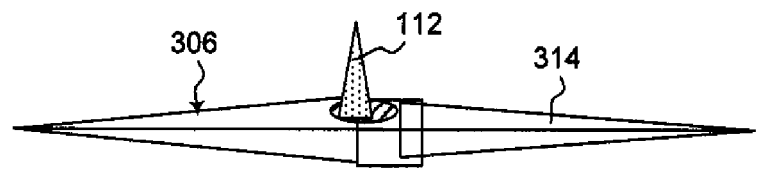
Figure 3C:
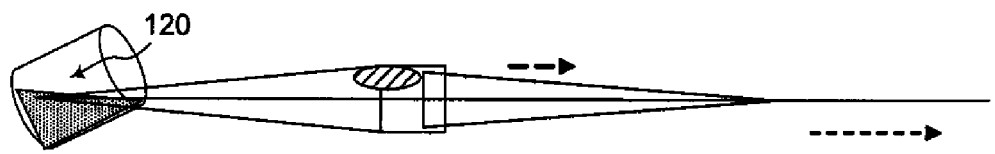
Figure 3D:
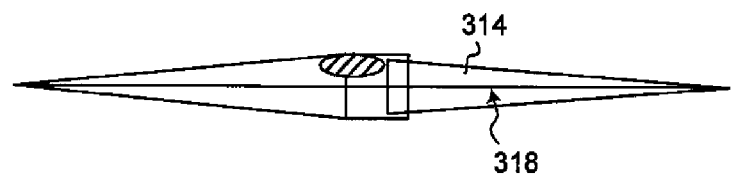
Figure 3E:
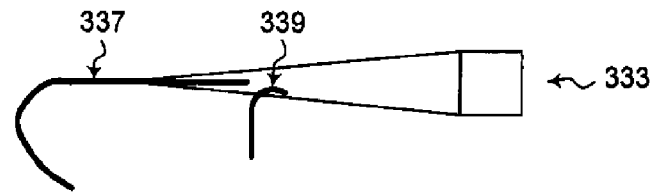
Figure 3F:
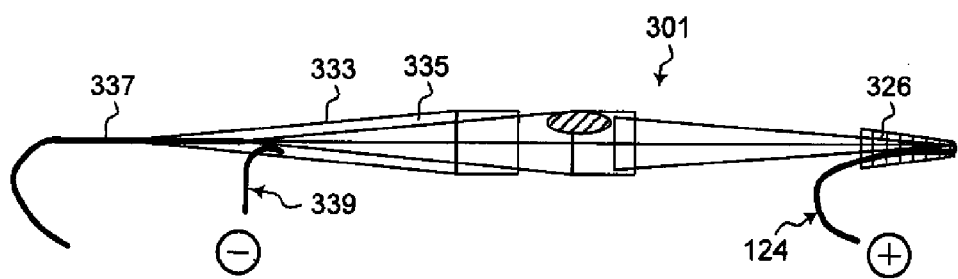

FIGS. 3A-3F illustrate another embodiment of a method for preparing an example of a microcapillary electrophoresis device 301 having a microchannel structure. In FIG. 3A, a vessel 300 has two micropipette tips 302 that are coupled together to form a vessel, and then formed into a microcapillary electrophoresis device 301. The ends of the tips 302 can be joined, or one can have its neck 304 snipped and slid into the neck 304 of the other tip, as shown. A wire 110 is extended from one end 311 to the other end 313. An opening 308 is formed in one of the tips 302. FIG. 3B shows a polymerizable composition 112 being introduced into an internal chamber 306 formed by the tips 302, which polymerizes into a polymeric body 314. FIG. 3C shows one end 311 of the vessel 300 being insert into a solvent 120 while the wire 110 is pulled from the other end 313 as shown by the dashed arrows. FIG. 3D shows the microchannel 318 formed by the polymeric body 314 as a result of removing the wire 110. FIG. 3E shows a micropipette tip 333 formed into or used as an electrode space 335 as shown in FIG. 3F. The tip 333 includes a working electrode 337 and a counter electrode 339 (cathode). The tip 333 is slid over the tip 302 to form the electrode space 335 that includes the working electrode 337 and the counter (cathode) electrode 339. The tip 302 includes an anode 124 that is held to the tip 302 with a fastener 326. Accordingly, the device in FIG. 3F can be used in microcapillary electrophoresis.

Figure 4A:
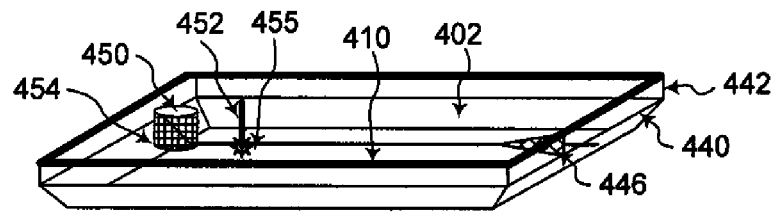
FIGS. 4A-4F illustrate an embodiment of a method for preparing an example of a microcapillary electrophoresis device having a microchannel structure.

FIGS. 4A-4F illustrate another embodiment of a method for preparing an example of a microcapillary electrophoresis device 401 having a microchannel structure. FIG. 4A shows a polymer substrate 440 having walls 442 attached that form an open vessel 402 (e.g., tray) with a large surface area basin and small height, although each can be modulated. A wire guide 446 is inserted through one of the walls 442 and a wire 410 is passed through the wire guide 446 into the open vessel 402. The wire 410 extends across to and is held by a wire holder 450. The substrate 440 includes two openings 454, 455; one opening 454 has the wire holder 450 and end of the wire 410 and another opening 455 is configured to receive an intermediate portion or loop of the wire 410. A tool 452 is used push the wire 410 into the opening 455.

Figure 4B:
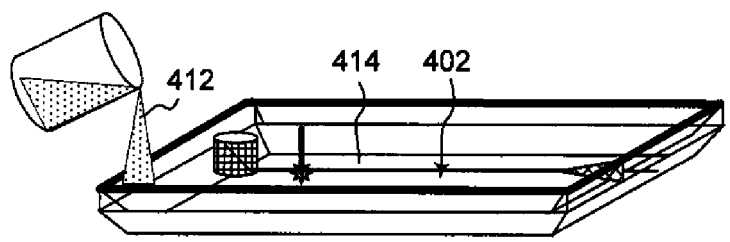

FIG. 4B shows a polymerizable composition 412 being introduced into the open vessel 402 and formation of polymeric body 414 around the wire 410.

Figure 4C:
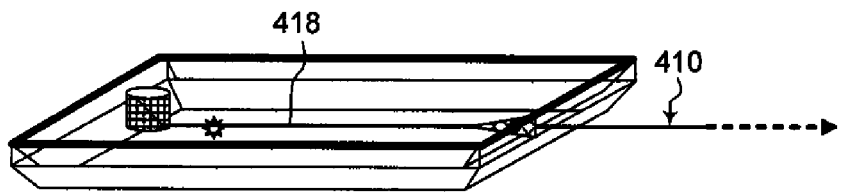

FIG. 4C shows the wire 410 being pulled from the polymeric body 414 in the direction of the dashed arrow and formation of the microchannel 418.

Figure 4D:
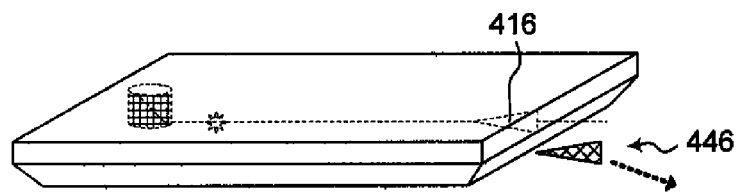

FIG. 4D shows the wire guide 446 being pulled from the polymeric body 414 in the direction of the dashed arrow and formation of the electrode space 416.

Figure 4E:
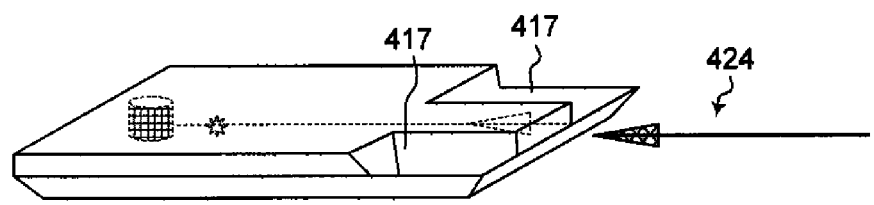

FIG. 4E shows insertion of an electrode 424 into the electrode space 416. Also shown are two additional electrode spaces 417.

Figure 4F:
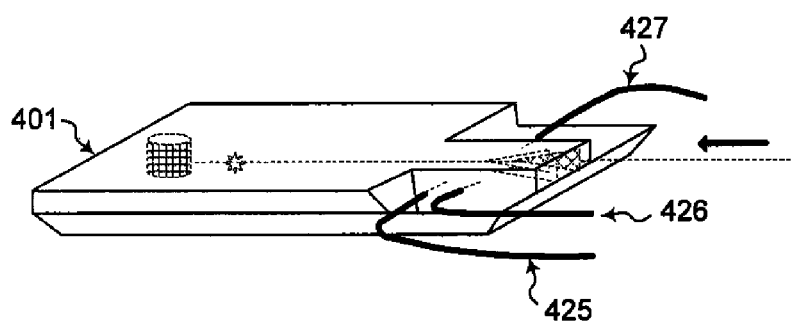

FIG. 4F shows additional electrodes 425, 426, 427 installed in the two electrode spaces 417 so as to be operably coupled with the electrode 424 in the electrode space 416. An electrophoresis electrode (not shown) can be located at the wire holder 450. Accordingly, the device in FIG. 4F can be used in microcapillary electrophoresis.

FIGS. 5A-5D illustrate another embodiment of a method for preparing an example of a microcapillary electrophoresis device 501 having a microchannel structure. In FIG. 5A, a vessel 502 has a basin 504 for receiving a polymerizable composition 512. The basin 504 can be formed from members 506 that also cooperate with a wire holder 508 to hold a wire 510. The wire 510 can be held up from or down on the basin 504.

FIG. 5B shows a polymerizable composition 512 being poured into the basin 504 and around the wire 510 and polymerized.

FIG. 5C shows the wire 510 being pulled from polymeric body 514 to leave the microchannel 518. The wire 510 can be either pulled straight out as shown by the arrow or lifted out to form a "U" shaped microchannel 518. FIG. 5D shows the polymeric body 514 having the microchannel 518 to form the microcapillary electrophoresis device 501. In this fabrication plan, a simple microchannel having, for example, a diameter of approximately 30 µm, can be fabricated with electrochemical detection approach.

Figure 6:
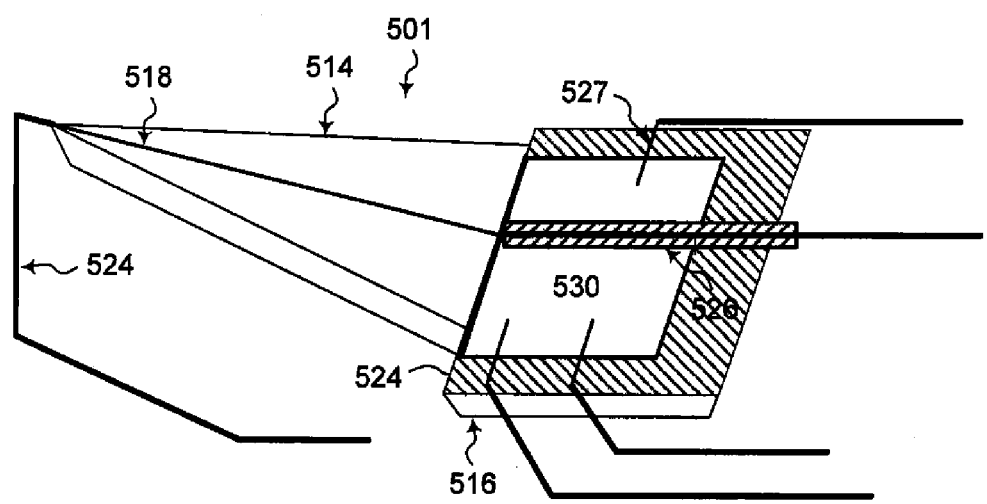
FIG. 6 illustrates an embodiment of a microcapillary electrophoresis device having a microchannel structure.

FIG. 6 illustrates an embodiment of a microcapillary electrophoresis device 501 having a microchannel structure. An electrode chip holder 516 coupled with counter 525, working 526, and reference 527 electrodes. One electrophoresis electrode 524 is coupled to the point of the polymeric body 514, and the other is coupled to the electrode chip holder 516. The electrode chip holder 516 also includes a buffer reservoir 530 that is connected to a microcapillary structure formed of a polymeric body 514 having a microchannel 518 that is configured for capillary electrophoresis. Accordingly, the device in FIG. 6 can be used in microcapillary electrophoresis.

In one embodiment, the microchannel structure having the microchannel can be formed with a material that is polymerizable, such as but not limited to, monomers, oligomers, or polymers that have siloxane or alkylsiloxane monomers. The monomers are then polymerized into polymers to form the polymeric body of the microchannel structure. For example, the microchannel structure can be prepared from a polyalkylsiloxane, such as polydimethylsiloxane. However, other polymerizable monomers or polymers prepared therefrom can be used, such as but not limited to, Siloxanes (PDMS), Natural Rubber (NR), Synthetic rubbers, Epoxy resin, PMMA, Polycarbonate, Polystyrene, and others.

This particular method is useful for making capillary electrophoretic chip devices using all types of elastomers, thermoplastic and thermosetting polymers. Here the monomer units (liquid state) in homopolymer or copolymers are allowed to polymerized around the microchannel shaping wire linearly coupled with working electrode alignment cavity shaping body unit, in to a non flow able viscous state and the wire and "working electrode alignment body" is pulled out of polymer leaving the channel and electrode cavity inside the semi-polymerized polymer and the polymer was finally allowed to be set completely.

The thermoplastic polymers (when they are in hot melted state) can be put around the "channel shaping wire" linearly coupled "working electrode alignment cavity" shaping body unit. The polymer cooled up to their viscous and non flow able, glass transition temperature to remove the wire and electrode to leaving behind the microchannel and working electrode cavities. The wire can also be heated up to that atemperature to make an easy release. The polymer is finally cooled up to room temperature to fully polymerize the polymer and finally the main electrodes were placed properly.

In one embodiment, the microchannel structure having the microchannel can be formed from a material that is crosslinkable, such as but not limited to, polymers and polysaccharides that can be crosslinked through curing or via a crosslinking agent. Examples include polymers or polysaccharides with reactive moieties (e.g., amines, carboxyls, etc.) that can crosslink one polymer strand with another polymer strand. Examples of polysaccharides that can be crosslinked can include celluloses, chitin, chitosan, or others.

The Polymer that can be crosslinked to form the microchannel includes SU8, Epoxy resins, Polycarbonates etc.

In one embodiment, the microchannel structure having the microchannel can be formed from a material that can form a body structure by combining or agglomerating loose materials into a solid body, such as but not limited to, polymeric beads, nanoparticles, microparticles, or other similar particle that can be molded, glued, sintered, or crosslinked together. For example, polymeric nanoparticles can be used to form the microchannel structure by melting, agglomerating, or sintering.

The microchannel structure can made by sintering or agglomerating polymeric powders around the wire and finally pulling the wire out to release the microchannel. For example polymer powder like Acrylic, Polystyrene, polyethylene, polypropylene, polystyrene, polyurethane, ultra high molecular weight polyethylene or polycarbonate powders etc can be used.

In one embodiment, a wire can be used as a microchannel forming member when the polymeric body is polymerized around the wire such that removal of the wire from the polymeric body leaves the microchannel substantially dimensioned as the wire. As such, the wire is a template for the microchannel shape. Also, the wire can be substituted with other microchannel forming members such as thread, filament, or any other elongate member having a suitable length and micron scale or smaller cross-sectional profile. Examples of the microchannel forming member used during a process for manufacturing a microchannel structure are shown in the figures. The microchannel forming member can be formed from a metal wire, fabric thread, glass filament, or the like. The microchannel forming member can have a cross-sectional profile with a diameter, width, or height that ranges from 1 nm to 100 microns, or 10 nm to 10 microns, or 100 nm to 1 micron.

The vessel can be any of a wide variety of vessels. The vessel can have any of a variety of shape and sizes with an internal chamber and two or more openings. The shapes can range from spherical to polygonal, and may be similarly shaped as any polymerization reaction vessel. The size of the polymerization vessel can range from microliter volumes, milliliter volumes, or centiliter volumes. Examples of polymerization vessels are shown in the figures. The vessel can be prepared from polymers, metals, glass, ceramics, composites, and any other suitable or compatible material for polymerization. For example, the vessel can be prepared from relatively stable polymers, such as polyolefins (e.g., polyethylenes and polypropylenes) or polyacrylates (e.g., polymethacrylates, polymethyl methacrylates, and the like). The metals can be any metal or alloy, such as stainless steel. The glass can be Pyrex or any borosilicate glass. The ceramics can be any suitable ceramic material ranging from alumina oxides to carbides, borides, nitrides, or silicates. Composite materials can be any suitable combination of polymers, metals, glasses, and ceramics.

The vessel can be prepared from a variety of existing structures, such as but are not limited to, one or more of containers, substrates, sheets, wafers, trays, syringes, needles, micropipette tips, micron scale tubes, molds, hoses, or combinations thereof. The vessel can be configured to have a fixed internal volume or a variable internal volume. The vessel can have an internal cavity larger than the polymeric body such that at least one portion of the internal cavity is devoid of the polymeric body. As such, the vessel internal cavity can have a void space and the polymeric body. The vessel can also have an internal cavity corresponding with the shape and size of the polymeric body. Additionally, the vessel can have one or more openings extending from an outer surface to an inner surface of an internal cavity.

Fabrication of the microchannel structure within the vessel as described above in connection with the figures can be consistent and repeatable and it can give substantially the same dimension microchannel structure every time. For example, the microchannel structure can be prepared from a polymerizable composition that is placed in the vessel and allowed to polymerize around the microchannel forming member (e.g., wire). A flexible and easily polymerizable polymer, such as PDMS can be beneficial in preparing the microchannel structure. Flexibility can be beneficial in terms of removing the wire from the microchannel structure as well as removing the microchannel structure from the vessel.

A wire can be positioned within the internal chamber of the polymerization vessel by being passed through an opening in the vessel through the internal chamber and out from another opening. The polymerizable composition can be introduced into the internal chamber of the vessel and around the wire. For example, the internal chamber can be filed with the polymerizable to a desired level or to a desired length of the wire so as to form a reservoir or space associated with the wire as shown in the figures. The polymer is allowed to semi-cure to a point where the wire can be pulled out of the semi-cured polymer to form a microchannel. The amount of curing can range depending on the polymer, but can be determined to be sufficiently cured to remove the wire when the curing polymer is shape stable. The wire can be pulled straight from the polymerizing polymer so as to leave a microchannel having substantially the same dimension as the wire. The microchannel is fluidly coupled with the reservoir such that a fluid that passes through the microchannel from one end can flow into the reservoir at the other end of the microchannel. The reservoir can receive electrodes and can be referred to as an electrode space. Also, the reservoir can retain an analyte or solution, or can have other uses depending on the use of the microchannel structure.

The withdrawal of the wire can be facilitated by the wire being coated with grease, such as but not limited to, silicone grease, fluoroether-based grease, hydrocarbon grease, or the like. Alternatively, the wire can be coated with a lubricant, such as but not limited to vegetable oils, fatty oils, hydrocarbons, graphites, or other lubricant. In another alternative, a swelling agent or solvent for the polymeric body of the microchannel structure can be used to facilitate withdrawal of the wire. Examples of a swelling agent or solvent are polymer specific, but can include with limitation chloroform, acetonitrile, dichloromethane, or water. The grease, lubricant, or swelling agent can ease the process of pulling and to avoid breakage of the wire or the polymeric body.

The electrodes for a microcapillary electrophoresis chip can be introduced at various points in the fabrication process, such as before, during, or after polymerization. The electrodes can be introduced into the vessel by one or more openings formed in the vessel wall.

The electrodes can be standard electrodes, which are electrically conducting. Examples of electrodes include but are not limited to cathodes, anodes, work electrodes, reference electrodes, or counter electrodes. For example, copper wire can be used as a working electrode, Ag/AgCl can be used as a reference electrode, and graphite rod and capillary tube electrodes can be used as a counter electrode.

In one embodiment, a microchannel structure can include a polymeric body defining a continuous surface of a seamless microchannel. The microchannel structure having the seamless microchannel can be formed of a single, unitary member so that there are no seams or junctions between multiple body pieces on the microchannel surface. Accordingly, the seamless microchannel can be a lumen within the polymeric body such that the seamless microchannel has all inner surfaces defined by the same polymeric body. The microchannel structure overcomes problems of microcapillary channels formed of multiple pieces because the continuous, seamless microchannel is less likely to rupture than a channel formed from multiple pieces adhered together. The one-piece polymeric body can include a first opening and a second opening of the seamless microchannel; however, more openings can be included depending on the configuration. Typically, a microchannel only has two openings, such as but not limited to an inlet and an outlet of the channel.

In one embodiment, the polymeric body of the microchannel structure can also define a reservoir or electrode space that is fluidly coupled with the seamless microchannel. The reservoir or electrode space is formed during the polymerization by leaving a space in the vessel around the wire that does not receive the polymerizing composition. For example, as shown in FIG. 2A, the polymerizable composition only partially fills the vessel such that the reservoir 16 is formed. The reservoir can be used to receive an analyte solution so as to be a reservoir. Alternatively, the reservoir can be used as a space for receiving electrodes to facilitate electrophoreses and/or analyte detection.

In one embodiment, the seamless microchannel is straight or linear without any bends. For example, the wire can be stretched across the internal chamber of the vessel so that the wire is taut and straight. After removal of the wire, the microchannel is similarly straight without any bends.

In one embodiment, the seamless microchannel has one or more bends between the microchannel openings (e.g., inlet and outlet). This results in the microchannel having one or more curves. For example, the wire can be inserted through the internal chamber of the vessel but left loose so that one or more bends form in the wire. Alternatively, the wire can be pre-bent with one or more curves. A flexible wire can allow for the wire to be extracted from the polymerizing composition while leaving behind a microchannel that has one or more bends in it.

In one embodiment, the seamless microchannel can have a substantially uniform cross-sectional profile. A uniform cross-sectional profile can be achieved with a wire that has a substantially uniform cross-sectional profile.

In one embodiment, the seamless microchannel can vary from narrower at one opening to wider at the opposite opening. For example, a wire can have a cross-sectional profile that increases along its length. The narrower end of the wire can be at a first opening of the microchannel with the wider end of the wire at the second opening. When the wire is extracted, it is pulled from the wider end at the second opening so that the narrow end is pulled through the microchannel.

The seamless microchannel can have a round or a polygonal cross-sectional profile, such as but not limited to a triangle, square, rectangle, pentagon, or the like. The shape of the cross-sectional profile can be obtained by selecting a wire having the same cross-sectional profile shape.

The polymeric body of the microchannel structure can define one or more seamless microchannels. The figures show embodiments where one wire is used to form a single microchannel in the microchannel structure. However, two or more wires can be used to form two or more microchannels.

The seamless microchannel can have a cross-sectional, radial, or longitudinal dimension, such as width, height, diameter, or the like, in the micron scale range or smaller. The cross-sectional dimension in the micron scale range can be submicron or from about 1 micron to about 1,000 microns. Examples include 10 microns, 50 microns, 210 microns, 300 microns, 500 microns, 750 microns and any range of sizes therebetween. Smaller wires that have cross-sectional dimensions less than 1 micron may be used to form nano scale channels, such as without out limitation from 1 nm to 900 nm, 10 nm to 500 nm, 25 nm to 250 nm, or 50 nm to 100 nm. The length of the microchannel can be configured as desired, and can range from 1 mm to 10 cm, 5 mm to 5 cm, or from 1 cm to 2.5 cm.

Using this method making channel less than 20 micron microchannel can be difficult because of lower tensile strength of many metals in those dimension as compared to bonding between wire and polymerized polymers. So there will be higher possibilities of breaking of wire inside the microchannel during the pulling of wire to release the microchannel and failure of the whole process. However the concept of a sacrificial wire or thread will be suitable. Where the Nylon thread can be used to shaping microchannels and latter can be dissolved with Dilute HCl to release microchannels.

The wire is removed from the polymeric body to provide the microchannel. To facilitate withdrawal of wire from the polymeric body, a lubricant or grease can be coated onto the wire before, during, or after polymerization. Also, a solvent for the polymeric body can be used to facilitate wire removal. For example, a solvent or swelling agent for the polymeric body can be introduced into the interface between the wire and polymeric body to allow the wire to be pulled out from the polymeric body. When the polymeric body is a polyalkylsilanol (e.g., polydimethylsiloxane), the solvent can be an organic solvent (e.g., chloroform).

The microchannel structure can be fabricated to include components of a microcapillary electrophoresis device. The components can include one or more electrodes that are operably coupled with the polymeric body and seamless microchannel. The electrodes can be located within a reservoir or electrode space that is fluidly coupled with the microchannel. The electrodes can be detection electrodes that are electronically operable, such as having a working electrode and counter electrode being operably coupled with the seamless microchannel (e.g., two electrode detection system). Also, a reference electrode can be operably coupled with the working and/or counter electrode. The reference electrode and working electrodes can be proximal with respect to each other with ends separated and adapted to detect current or voltage. A three-electrode detection system can include working, reference, and counter electrodes, with the working electrode being closest to the microchannel opening. The working and reference electrodes being positioned at or just beyond the opening of the microchannel or in the reservoir or electrode space. The detection electrodes can be configured such that: the working electrode is biased relative to the reference electrode; and/or the counter electrode completes the circuit.

The components can also include electrophoretic electrodes that can be removable or coupled with a microchannel structure and/or vessel. The electrophoretic electrodes can be operably coupled with each opening end of the microchannel. The electrophoretic electrodes can include an anode and a cathode which can be separated by the microchannel with either electrode being at either opening. In one aspect, the anode is located at an entrance of the microchannel, and the cathode is located at the exit of the microchannel. In one option, the cathode (−) is positioned closer to the working, counter, and/or reference electrodes. In another option, the anode (+) is positioned closer to the working, counter, and/or reference electrodes. In one option, the counter electrode is the cathode.

The polymeric body can have one or more openings aligned with the one or more openings in the vessel. The aligned openings can provide for alignment of electrodes within the vessel and electrode space. Accordingly, the electrodes can extend into a reservoir defined by the vessel and polymeric body. The electrodes can also be affixed in the one or more openings with adhesive, such as but not limited to, acrylic adhesive, silicone adhesives, isobutylene adhesives or other contact adhesives or other fixing agent, such as but not limited to, tape, glue, friction, or others. Also, a fluid tight seal can be used to hold the electrodes in the openings.

The polymeric body can be operably coupled with detection electrodes and electrophoresis electrodes so as to be configured for capillary electrophoresis and detection of analytes. The configuration can include electrophoresis and detection electrodes operably coupled with the microchannel. One or more of the electrodes can be held by an electrode holder, such as in a reservoir. For example, the detection electrodes can be in the reservoir. The electrophoresis electrodes can be located at opposite ends of the microchannel.

The electrodes can be operably coupled with a computing system. The computing system can be configured for receiving electronic data from the detection electrode. Also, the computing system can be configured for receiving and/or transmitting electronic data with the electrophoresis electrodes. The computing system can have data computing components comprising code for executable instructions for operating with the one or more electrodes by, for example, modulating properties of electronic flow between the electrophoresis electrodes; determining properties of electronic flow between the electrophoresis electrodes; performing voltometry, conductometry, amperometry or potentiometry or combinations thereof; receiving and/or recording data for voltometry, conductometry, amperometry or potentiometry or combinations thereof; or the like. The computing system can also provide instructions that include obtaining measurements of voltometry, conductometry, amperometry or potentiometry or combinations thereof.

Additionally, the electrophoresis electrodes can be couplable with a power supply. Standard electrophoresis electrode configurations and adaptations are also included.

A method of manufacturing a microchannel structure can include providing a vessel having a body defining an internal chamber that has at least a first opening and a second opening; introducing a micron scale dimensioned wire within the internal chamber; polymerizing a polymerizable composition within the internal chamber around the wire; removing the wire from the polymerizable composition before fully polymerized so as to leave a microchannel; and finishing polymerization to form a polymeric body defining the microchannel.

Additionally, a vessel can be provided or manufactured that has a body defining an internal chamber that has a first opening and a second opening. The method of manufacture can also include forming the first and second opening. In some instances, the vessel has one or more openings that are closed with a cap or seal, and the method can include removing the cap or seal during manufacturing for introducing the wire, polymerization material, or electrodes. The vessel can be selected with an inner surface defining one or more exterior surfaces of the polymerizable material.

In one option, the vessel can be formed from one or more of containers, substrates, sheets, wafers, trays, syringes, needles, micropipette tips, micron scale tubes, molds, hoses, or combinations thereof.

The vessel can be configured to have a fixed internal volume. Alternatively, the vessel can be configured to have a changeable or variable internal volume. As such, during the manufacture, the method can include changing the volume of the vessel before, during or after introducing a polymerizable composition into the internal chamber; and/or changing the volume of the vessel before, during or after polymerizing the polymerizable composition within the internal chamber; and/or changing the volume of the vessel before, during or after introducing the wire into the internal chamber.

The vessel can have an internal cavity larger than the polymeric body such that at least one portion of the internal cavity is devoid of the polymerizable composition. This portion can be configured into an electrode holder or electrode space. Accordingly, the method can include partially or fully filling the internal cavity with the polymerizable composition.

The vessel can be provided with one or more openings, or the method of manufacture can include forming one or more openings extending from an outer surface of the vessel to an inner surface of the internal cavity. In some instances, the method can include aligning the one or more openings of the vessel with one or more openings of the polymeric body.

During placement of the wire, the method can include extending and/or securing a wire from a first opening of the vessel across the internal chamber to a second opening. This can include extending and securing a wire across the internal chambers. Also, the method can include obtaining the wire; preparing the wire; positioning the wire to be straight; positioning the wire to have one or more bends; positioning one or more wires to have one or more intersections; positioning one or more wires to have two or more branches, where the wire has a substantially uniform cross-sectional profile, a round cross-sectional profile, or a polygonal cross-sectional profile.

The formation of the polymeric body can include polymerizing a polymerizable composition within the internal chamber and around the wire. The polymerization can be by light induced polymerization. Polymerization via light can be performed with a polymerizable composition that includes a photoinitiator that can initiate polymerization of acrylic monomers, epoxy monomers, vinyl ethers, and others when exposed to light. Non-limiting examples of photoinitiators can include azobisisobutyronitrile (AIBN), benzoyyl peroxide, 2,2-dimethoxy-2-phenylacetophenone (DMPA), polyethylene glycol diacrylate (PEGDA), trimethylolpropane triacrylate (TPT), and acryloyl chloride. Light having the appropriate wavelength to activate the photoinitiator can then induce polymerization.

Formation of the microchannel can include removing the wire from the polymerizable composition before full polymerization so as to leave a microchannel. This can include pulling the wire from the polymerizable composition to leave a seamless microchannel as a lumen within the polymeric body. For example, after some polymerization, the wire can be removed from the polymeric body. To facilitate removal of the wire, one of the openings in the vessel can be inserted into a solution of a swelling agent before removing the wire. The swelling agent can then allow for the wire to be withdrawn without compromising the structural integrity of the seamless microchannel. Alternatively, a lubricant can be used in place of the swelling agent.

The polymerization can also form a reservoir electrode space with the microchannel. This can include: inserting an electrode space member into the vessel before, during or after the polymerizable composition; inserting an electrode space member into the vessel before, during or after the wire; removing the electrode space member from the vessel before, during or after the polymerizable composition; evacuating the electrode space; at least partially filling the electrode space and/or microchannel with a fluid, where the fluid is a electrolyte solution, aqueous solution, solvent, inert gas, air, oxygen, nitrogen, or the like; pressurizing the microchannel; at least partially filling the electrode space and/or microchannel with a second polymerizable composition, where optionally, the second polymerizable composition is different from the first polymerizable composition; at least partially filling the electrode space and/or microchannel with a conductive composition.

The manufacture process can also include finishing the polymerization to form the polymeric body defining the microchannel. The polymerization can be finished by merely allowing polymerization to continue, or to induce additional polymerization. For example, the polymerization reaction may continue as the wire is being pulled from the polymerizing composition by simply allowing the polymerization to continue. In another example, light that activates a photoinitiator can be extinguished prior to withdrawal of the wire from the polymerizing composition, and then the light can be illuminated again to continue the polymerization.

The manufacture process can also include forming electrodes as described herein. The electrodes can be electron-conducting metals such as copper, platinum, gold, or others. Examples of electrode manufacture processes are provided in the examples below.

The manufacture process can include providing a vessel having a body defining an internal chamber that has a first opening and a second opening; extending a micron scale dimensioned wire from the first opening across the internal chamber to the second opening; partially polymerizing a polymerizable composition within the internal chamber around the wire; removing the wire from the polymerizable composition before full polymerization so as to leave a microchannel; positioning one or more electrodes within the internal chamber so as to be operably coupled with the microchannel; and completing polymerization to form a polymeric body defining the microchannel.

The microchannel structure can also be included with a microcapillary electrophoresis device or system. The preparation of the microcapillary electrophoresis device or system can include inserting the microchannel structure into a microcapillary electrophoresis device or system components; combining the microchannel structure with capillary electrophoresis components; and/or forming a capillary electrophoresis device with the microchannel structure.

The manufacture of a microcapillary electrophoresis device or system can include operably coupling one or more electrodes (e.g., electrophoresis or detection) with the polymeric body and/or seamless microchannel and functional positioning of the same. The electrodes can be electronically operable electrodes prepared with the microchannel structure as follows: the electrodes being a working electrode and counter electrode in a two electrode detection system; including a reference electrode to be operably coupled with the working and/or counter electrode; positioning the reference electrode and working electrodes proximal with each other with ends separated and adapted to detect current or voltage or the like; positioning a three electrode detection system with working, reference, and counter electrodes, with the working electrode closes to the microchannel exit; positioning the working and reference electrodes at or just beyond the opening of the microchannel, at or beyond the exit of the microchannel, or at or beyond the opening of the microchannel into an electrode reservoir; positioning the detection electrodes in the electrode reservoir, where the electrode reservoir has one electrophoresis electrode and the working electrode is biased relative to the reference electrode; a counter electrode to complete the circuit; electrophoretic electrodes operably coupled with each end of the microchannel, where the electrophoretic electrodes include an anode and a cathode, the anode being located at an entrance of the microchannel and the cathode being located at the exit of the microchannel; the cathode being positioned closer to the working, counter, and/or reference electrodes; the anode being positioned closer to the working, counter, and/or reference electrodes; and/or the counter electrode being the cathode.

One method of manufacturing a microcapillary electrophoresis structure can include forming the microchannel structure within an internal chamber of a vessel and positioning one or more electrodes within the internal chamber so as to be operably coupled with the microchannel. The method can also include forming an electrode receiving opening in the vessel before, during or after polymerization; forming the opening with a drill, punch, hot wire, laser, or the like; electronically coupling one or more of the electrodes with an electronic controller; electronically coupling one or more of the electrodes with a computing system; electronically coupling one or more of the electrodes with high voltage power supply; coupling the microchannel structure with an electrode holder; and/or coupling the microchannel structure with an analyte reservoir.

One method of manufacturing a microcapillary electrophoresis structure can include providing a vessel having a body defining an internal chamber that has a first opening and a second opening; extending a micron scale dimensioned wire from the first opening across the internal chamber to the second opening; polymerizing a polymerizable composition within the internal chamber around the wire; removing the wire from the polymerizable composition before fully polymerized so as to leave a microchannel; positioning one or more electrodes within the internal chamber so as to be operably coupled with the microchannel; and finishing polymerization to form a polymeric body defining the microchannel. This method can also be modified as described herein.

One embodiment of a microcapillary electrophoresis device or system can include a microchannel structure; and one or more microcapillary electrophoresis components operably coupled with the microchannel structure.

Microcapillary electrophoresis components can include one or more electrodes; detection electrodes; electrophoresis electrodes; an electrode holder; a microcapillary structure holder; an analyte reservoir container; an analyte composition; a vessel; a high voltage power supply; a controller; a computing system; software or other memory device having computer executable instructions for performing electrophoresis with the microcapillary structure.

A microcapillary electrophoresis kit can include a microcapillary structure and one or more of the microcapillary electrophoresis components.

The microchannel structures can be used in various methods of detecting an analyte. Such a method can include providing the microchannel structure associated with a microcapillary system (e.g., coupled or couplable); electrophoresing an analyte through the microchannel; and detecting an electronic property of the analyte. The detection method can further include modulating properties of electronic flow between the electrophoresis electrodes; determining properties of electronic flow between the electrophoresis electrodes; performing voltometry, conductometry, amperometry or potentiometry or combinations thereof; receiving and/or recording data for voltometry, conductometry, amperometry or potentiometry or combinations thereof; or the like.

EXAMPLES

The following examples are presented to illustrate various techniques for implementing the microchannels, methods, and other aspects and features described herein. These examples are presented solely for purposes of illustration and are not to be limiting of the disclosed embodiments.

According to a first example, Poly(dimethylsiloxane) (Sylgard 184, Dow Corning) is used to fabricate microchannel structure. Silver, Tungsten, Copper, various gauge transformer wire as well as nylon wire is used to shape the microchannel. Vacuum grease or a swelling/solvent agent, such as chloroform, is used to release the wire or nylon thread from the polymeric body. Sheets formed from poly(methyl methacrylate) (PMMA), silicon wafers, and polyethylene containers as well as syringes, micropipette tips, syringe-needles, or the like, are used to cast the polymeric body.

The working electrode in this first example is constructed with a 210 μm diameter Cu wire. A 2 cm long glass capillary with less than 1 mm outside diameter is introduced into the end of a 7 cm long glass capillary tube (1 mm inside diameter). A Cu wire is then inserted into the inner glass capillary until it protrudes approximately 2-3 mm from the tip. Epoxy glue is applied to the tip of the capillary in order to seal the Cu wire and fix the inner capillary to the outer tube. The other end of the wire is also sealed to support the electrical connection. Before use, the electrode surface is wet polished with 0.05 μm alumina powder, rinsed with a stream of deionized water, and cleaned ultrasonically for 5 minutes. Prior to use, the working electrode is scanned between 0 and 0.4 V against the Ag/AgCl (3.0 M KCl; CH Instruments, Austin, Tex., USA) reference electrode in test medium until a stable cyclic voltammogram is obtained.

A graphite lead electrode can be prepared according to this example. A 0.5 mm inner diameter glass capillary is pulled to form a tip of about 300 μm diameter. Then a 300 μm pencil lead (Faber Castle, Polymer fine lead) is inserted into the tip of the pulled glass capillary and sealed with epoxy. A Cu wire is inserted in the other end of the glass capillary and is contacted with the pencil lead by soldering tin. Before use, the electrode is polished and ultrasonically cleaned.

An example of a manufacture process can include stretching a wire between a sealed syringe tip and an opening in a piston of a polypropylene syringe. PDMS (Sylgard 184) elastomer prepolymer liquid is poured into the syringe and cross-linked by curing it at 70° C. for about 40 minutes. The wire is removed from the semi-cured PDMS block by pulling the wire, while keeping the syringe tip in chloroform to provide a microchannel. The PDMS is cured for another 40 minutes at 70° C. and the electrochemical detection electrodes are inserted through the piston into the electrode space after proper alignment. The electrochemical detection electrodes are inserted into the electrode space after proper alignment through an alignment wire, operably coupling the counter electrode with the working electrode and operably coupling electrophoresis electrodes with the microchannel.

In another example, polypropylene syringes of 5 ml capacity and 8 cm length are used as vessels. The syringe piston has an opening formed in a line with the syringe tip aperture. Tungsten wire of 50 um diameter is stretched across the syringe tip and the piston opening with cellophane tape. Sylgard 184 elastomer is mixed with the curing agent with 10:1 or 9:1 by weight ratio depending upon the experimental condition. The resulting mixture is poured in the syringes through the piston opening. A curing process is applied for 16 to 18 hours at room temperature or at 65-70° C. for about 35 to 40 minutes. A cylindrical wall of the syringe has an opening formed laterally at the point where PDMS upper layer ends. An electrode is inserted in a direction up to the point where the wire exits the set PDMS block and is fixed with syringe wall using, for example, epoxy glue. The microchannel-forming wires can be removed while dipping the wire endings on both ends in chloroform. The microchannel is cured for another 16 to 18 hours at room temperature or for about 40 minutes at 70° C.

An example of a cost-effective electrochemical detection microcapillary electrophoresis chip can include stretching a wire between a sealed syringe tip and a micropipette tip inserted in an opening in a piston of a polypropylene syringe. Sylgard 184 elastomer prepolymer liquid is poured into the piston and cross-linked by curing at about 70° C. for about 40 minutes. The wire is removed from the resulting semi-cured PDMS block by pulling while keeping the syringe tip in chloroform. The polymer composition is cured for about another 40 minutes at about 70° C. Electrochemical detection electrodes are attached from the piston side using micropipette tip slots. A counter electrode that functions as cathode is also attached along with an anode electrophoresis electrode.

In another example, two polyethylene micropipette tips are joined base to base, so as to form a reservoir for PDMS casting. A tungsten wire of 50 um diameter is inserted through one tip and stretched across to the other tip. An opening is created on a wall of micropipette tip, and a PDMS prepolymer curing agent mixture is passed through the opening into the micropipette reservoir. Sylgard 184 elastomer is mixed with the curing agent with 10:1 or 9:1 by weight ratio is poured into the micropipette reservoir through the opening. A curing process is performed for about 16 to 18 hours at room temperature or at about 65-70° C. for about 35 to 40 minutes. The wire is removed while dipping the wire endings on both ends in chloroform to form the microchannel. The polymeric body having the microchannel is cured for another 16 to 18 hours at room temperature or about 40 minutes at about 70° C. A detection reservoir micropipette tip has an electrode inserted through its tip opening. The electrode is aligned with tip of micropipette microchannel by placing the detection reservoir base over the tip of micropipette vessel containing the microchannel and then attaching the detection reservoir micropipette tip to the micropipette vessel using epoxy or another adhesive. A platinum electrode for electrophoresis and counter electrode is inserted and fixed in the detection reservoir by forming a through hole and using epoxy or adhesive.

In another example, a 5 cm×3 cm PMMA sheet can be used to fabricate an electrochemical detection microcapillary electrophoresis chip. A hole of 4 mm diameter and another hole of 0.8 mm diameter (i.e., an injection point) are formed in midline at one end of the PMMA sheet with a 1 cm distance. A tip portion of micropipette tip of 1 cm length is used for electrode alignment space. The micropipette tip base is cut to a size of 4 mm OD and 5 mm length and is inserted in the 4 mm diameter hole and configured to be used as a reservoir. Tungsten wire (diameter 50 um) is passed through the micropipette tip reservoir and tip and stretched across the PMMA substrate in the midline. A wooden toothpick can be used to press the wire through the 0.8 mm diameter hole in the PMMA sheet. Accordingly, wire is stretched between the three points of the reservoir end, injection point, and electrode of polypropylene tube. Sylgard 184 elastomer is mixed with the curing agent with 10:1 or 9:1 by weight ratio and is poured in the PMMA sheet around the wire and cured for about 16 to 18 hours at room temperature or at about 65 to 70° C. for about 35 to 40 minutes. The wire is removed while dipping both of the wire ends in chloroform to form the microchannel. The polymer is cured for another 16 to 18 hours at room temperature or for about 40 minutes at 70° C. The tip portion of the micropipette tip is removed, leaving space for placing an electrode in line with the microchannel. A buffer waste reservoir is formed, and the electrodes are affixed.

In another example, fabrication of a cost-effective electrochemical detection based microcapillary electrophoresis chip can include passing a tungsten wire (diameter 50 um) through a micropipette tip reservoir and tip and stretching it across the middle section of a PMMA sheet. A wooden toothpick is used to press the wire through a 0.8 mm diameter injection hole in the PMMA sheet. Sylgard 184 elastomer is mixed with the curing agent (10:1 by weight) degassed and the resulting elastomer prepolymer liquid is poured on the PMMA sheet and cross-linked by curing it at about 70° C. for about 40 minutes. The wire is pulled from the semi-cured PDMS. The PDMS is cured for about another 40 minutes at about 70° C. The tip is removed for an electrode space, and the electrodes are aligned. A working electrode, counter electrode, and electrophoresis electrodes are attached after a space for a buffer waste reservoir is cut from a rear end of the channel.

In yet another example, a triangular piece of PMMA (with two equal 7 cm sides and one 4 cm base side) sheet is prepared. Transformer wire of 49 gauge (30 µm) is stretched across the PMMA between from the base to a vertex of the triangle. The periphery of the PMMA triangular sheet is enclosed with cellophane tape. The wire is stretched on the PMMA sheet and is pressed with a glass slide to keep the wire near to the PMMA sheet. Pre-polymer and curing agent mixture (9:1) is poured on the PMMA sheet around the wire and is allowed to cure at about 70 to 75° C. for about 30 to 35 minutes. After curing, the wire is pulled out or peeled up off of the PDMS, so as to provide a closed or open microchannel, respectively. The bottom portion of the microchannel can be further reinforced by sealing it with another PDMS block using plasma asking. It can be also bonded reversibly to another PDMS flat block by pressing it against the other block. Another way for sealing the channel is to the mixed polymer over the bottom of the channel and to cure for about 70 to 75° C. for about one hour.

To couple the electrodes with the end of the microchannel, an electrode holder is prepared from a PMMA sheet in this example. The electrode holder has holding sites for the working electrode, the counter electrode, the reference electrode, and the electrophoretic electrode.

The microcapillary structure can be used with a variety of capillary electrophoresis (CE) protocols, including those that encompass a family of related separation techniques that use narrow-bore fused-silica capillaries to separate a complex array of large and small molecules. High electric field strengths are used to separate molecules based on differences in charge, size and hydrophobicity. Sample introduction is accomplished by immersing the end of the capillary into a sample vial and applying pressure, vacuum or voltage. Depending on the types of capillary and electrolytes used, the technology of CE can be segmented into several separation techniques. Examples of these include:

Capillary Zone Electrophoresis (CZE), also known as free-solution CE (FSCE), is the simplest form of CE. The separation mechanism is based on differences in the charge-to-mass ratio of the analytes. Fundamental to CZE are homogeneity of the buffer solution and constant field strength throughout the length of the capillary. The separation relies principally on the pH controlled dissociation of acidic groups on the solute or the protonation of basic functions on the solute.

Capillary Gel Electrophoresis (CGE) is the adaptation of traditional gel electrophoresis into the capillary using polymers in solution to create a molecular sieve also known as replaceable physical gel. This allows analytes having similar charge-to-mass ratios to be resolved by size. This technique is commonly employed in SDS-Gel molecular weight analysis of proteins and the sizing of applications of DNA sequencing and genotyping.

Capillary Isoelectric Focusing (CIEF) allows amphoteric molecules, such as proteins, to be separated by electrophoresis in a pH gradient generated between the cathode and anode. A solute will migrate to a point where its net charge is zero. At the solutes isoelectric point (pI), migration stops and the sample is focused into a tight zone. In CIEF, once a solute has focused at its pI, the zone is mobilized past the detector by either pressure or chemical means. This technique is commonly employed in protein characterization as a mechanism to determine a protein's isoelectric point.

Isotachophoresis (ITP) is a focusing technique based on the migration of the sample components between leading and terminating electrolytes. Solutes having mobilities intermediate to those of the leading and terminating electrolytes stack into sharp, focused zones. Although it is used as a mode of separation, transient ITP has been used primarily as a sample concentration technique.

Electrokinetic Chromatography (EKC) is a family of electrophoresis techniques named after electrokinetic phenomena, which include electroosmosis, electrophoresis and chromatography. A key example of this is seen with cyclodextrin-mediated EKC. The differential interaction of enantiomers with the cyclodextrins allows for the separation of chiral compounds. This approach to enantiomer analysis has made significant impact on the pharmaceutical industry's approach to assessing drugs containing enantiomers.

Micellar Electrokinetic Capillary Chromatography (MECC OR MEKC) is a mode of electrokinetic chromatography in which surfactants are added to the buffer solution at concentrations that form micelles. The separation principle of MEKC is based on a differential partition between the micelle and the solvent. This principle can be employed with charged or neutral solutes and may involve stationary or mobile micelles. MEKC has great utility in separating mixtures that contain both ionic and neutral species, and has become valuable in the separation of very hydrophobic pharmaceuticals from their very polar metabolites.

Micro Emulsion Electrokinetic Chromatography (MEEKC) is a CE technique in which solutes partition with moving oil droplets in buffer. The microemulsion droplets are usually formed by sonicating immicible heptane or octane with water. SDS is added at relatively high concentrations to stabilize the emulsion. This allows the separation of both aqueous and water-insoluble compounds, and is used effectively by the pharmaceutical industry as generic methodology to analyze a broad spectrum of pharmaceuticals.

Non-Aqueous Capillary Electrophoresis (NACE) involves the separation of analytes in a medium composed of organic solvents. The viscosity and dielectric constants of organic solvents affect both sample ion mobility and the level of electroosmotic flow. The use of non-aqueous medium allows additional selectivity options in methods development and is also valuable for the separation of water-insoluble compounds.

Capillary Electrochromatography (CEC) is a hybrid separation method that couples the high separation efficiency of CZE with HPLC and uses an electric field rather than hydraulic pressure to propel the mobile phase through a packed bed. Because there is minimal backpressure, it is possible to use small-diameter packings and achieve very high efficiencies. Its most useful application appears to be in the form of on-line analyte concentration that can be used to concentrate a given sample prior to separation by CZE.

One skilled in the art will appreciate that, for these and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim 1ncludes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

We claim:

1. A method of manufacturing a microchannel structure, the method comprising:
   providing a vessel having a body defining an internal chamber that has at least a first opening and a second opening;
   introducing a micron scale dimensioned wire into the internal chamber;
   polymerizing a polymerizable composition within the internal chamber around the wire;
   removing the wire from the polymerizable composition before substantially full polymerization thereof to thereby leave only the polymerizable composition in the internal chamber prior to completing the polymerization; and
   completing the polymerization polymerizable composition to form a polymeric body defining a seamless microchannel having a smooth, continuous surface without any junctions.

2. The method of claim 1, comprising providing a vessel having a body defining an internal chamber that has a first opening and a second opening.

3. The method of claim 1, comprising forming first and/or second openings in the vessel.

4. The method of claim , comprising removing or breaking a seal at first or second openings of the vessel.

5. The method of claim 1, comprising introducing the polymerizable composition into the vessel through the first or the second opening.

6. The method of claim 1, comprising forming an electrode space between the vessel and polymerizable composition.

7. The method of claim 1, comprising inserting a medium into an opening in the vessel before removing the wire, the medium being configured for facilitating removal of the wire from the polymerizable composition.

8. The method of claim 1, comprising extending and securing the wire across the internal chamber.

9. The method of claim 1, comprising positioning the wire to be substantially straight.

10. The method of claim 1, comprising positioning the wire to have one or more bends.

11. The method of claim 1, comprising positioning one or more wires to have one or more intersections or have two or more branches.

12. The method of claim 1, wherein the wire has a substantially uniform cross-sectional profile.

13. The method of claim 1, comprising inserting a medium into an opening in the vessel before removing the wire, the medium being configured for facilitating removal of the wire from the polymerizable composition.

\* \* \* \* \*

UNITED STATES PATENT AND TRADEMARK OFFICE
CERTIFICATE OF CORRECTION

PATENT NO. : 8,715,558 B2  
APPLICATION NO. : 13/257948  
DATED : May 6, 2014  
INVENTOR(S) : Prabhakar et al.

It is certified that error appears in the above-identified patent and that said Letters Patent is hereby corrected as shown below:

On the Title Page

On Page 2, Item (56), under "OTHER PUBLICATIONS", in Column 2, Line 4, delete "Electrophoreses" and insert -- Electrophoresis --, therefor.

In the Drawings

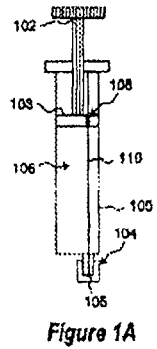

In Sheet 1 of 11, above Figure 1B, insert Figure --  Figure 1A  --.

In the Specification

In Column 9, Line 11, delete "atemperature" and insert -- a temperature --, therefor.

In Column 11, Line 44, delete "reservoir 16" and insert -- reservoir --, therefor.

In Column 11, Line 47, delete "electrophoreses" and insert -- electrophoresis --, therefor.

In Column 19, Line 58, delete "asking." and insert -- ashing. --, therefor.

In Column 21, Line 2, delete "immicible" and insert -- immiscible --, therefor.

Signed and Sealed this  
Thirtieth Day of September, 2014

Michelle K. Lee  
*Deputy Director of the United States Patent and Trademark Office*

CERTIFICATE OF CORRECTION (continued)
U.S. Pat. No. 8,715,558 B2

In Column 22, Line 13, delete "and or" and insert -- and/or --, therefor.

In Column 23, Line 32, delete "1ncludes" and insert -- includes --, therefor.

In the Claims

In Column 24, Line 55, in Claim 4, delete "claim," and insert -- claim 1, --, therefor.